United States Patent [19]

Nelson

[11] Patent Number: 4,520,926

[45] Date of Patent: Jun. 4, 1985

[54] CONTAINER FOR SHARPS

[75] Inventor: Ralph E. Nelson, Newport Beach, Calif.

[73] Assignee: Winfield Corp., San Diego, Calif.

[21] Appl. No.: 583,599

[22] Filed: Feb. 27, 1984

[51] Int. Cl.³ .................... A61M 5/32; B02C 19/12
[52] U.S. Cl. .................................. 206/366; 206/370;
206/63.5; 220/375
[58] Field of Search ............ 206/366, 370, 63.5,
206/525, 380, 18; 220/375, 94 A

[56] References Cited

U.S. PATENT DOCUMENTS

| 357,421 | 2/1887 | Spencer | 206/63.5 |
| 3,145,872 | 8/1964 | Hayes | 220/375 |
| 4,454,944 | 6/1984 | Shillington et al. | 206/366 |

*Primary Examiner*—William T. Dixson, Jr.
*Attorney, Agent, or Firm*—Ellsworth R. Roston; Charles H. Schwartz

[57] ABSTRACT

A container for holding sharp objects includes a bottle having a body and a rim extending upwardly from the body and defining an opening into the body. A cap is disposed upon the rim in abutting relationship to the rim near the bottom of rim. The rim and the cap define a detent relationship to hold the cap in irremovable relationship on the rim. A funnel made from a relatively soft and pliant material is disposed on the rim between the cap and the rim in sealed relationship with the cap and the rim. The funnel and the rim define a detent relationship to hold the funnel on the rim. The funnel is provided with a portion extending downwardly and inwardly into the opening in the rim at an angle to the rim. The inwardly extending portion is slitted to define a plurality of resilient leaves. The funnel abuts the rim and the cap along the side and top of the rim and the cap. The top of the rim is shaped to define a fulcrum for pivotal movements of the funnel leaves in accordance with the transfer of the sharp objects into the bottle through the opening in the rim of the bottle. When the cap is inserted on the rim, the rim, the funnel and the cap define a permanently sealed relationship to prevent sharp objects from being removed from the bottle.

30 Claims, 6 Drawing Figures

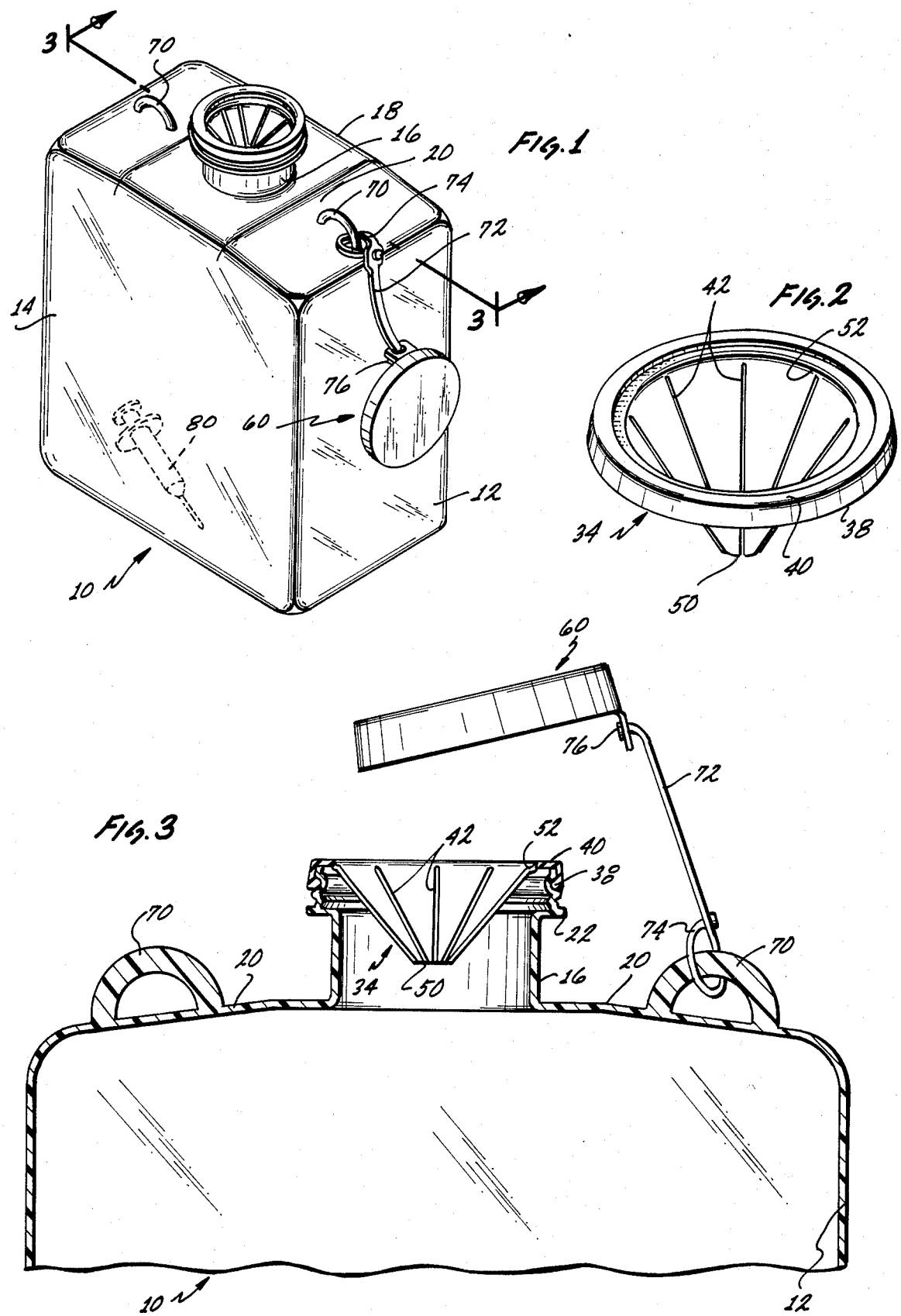

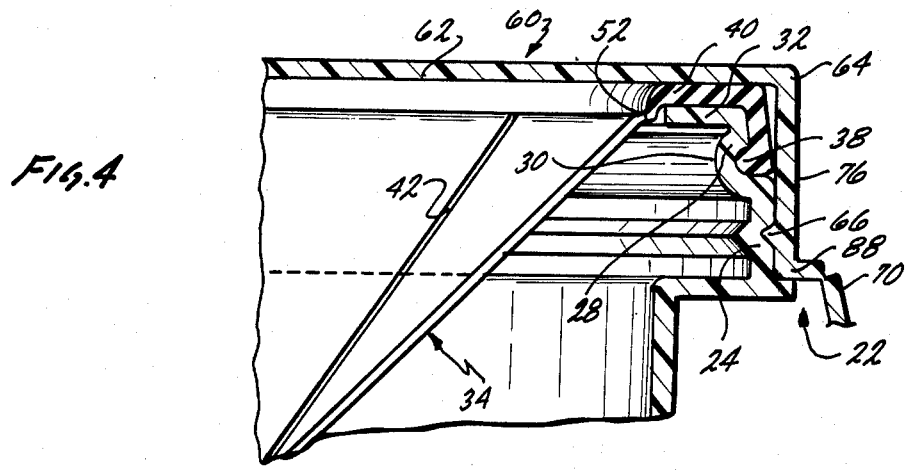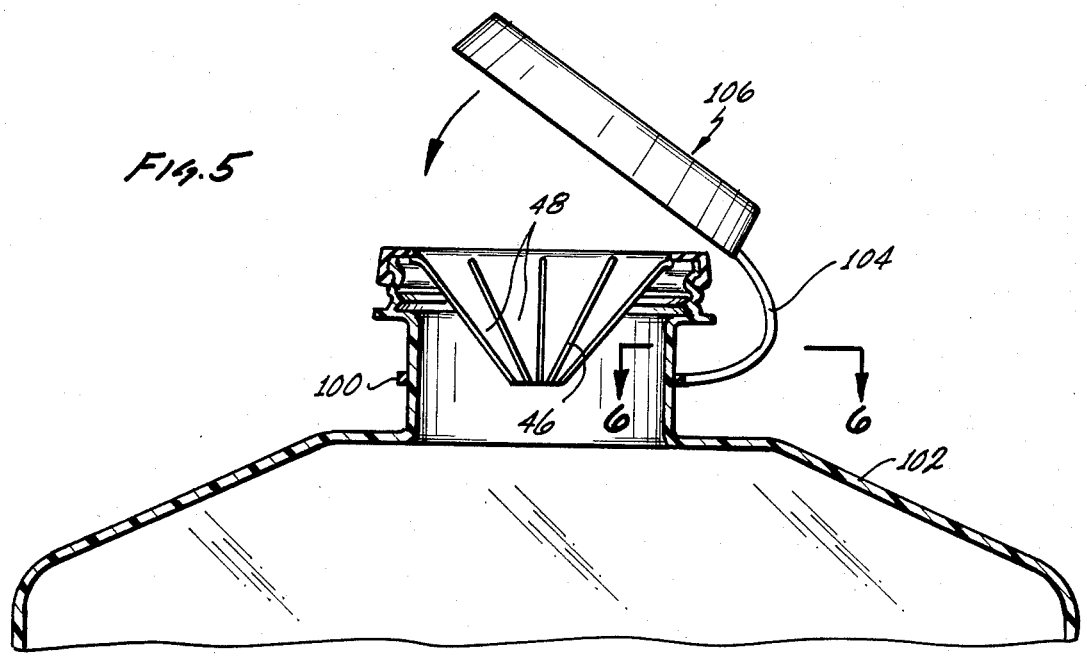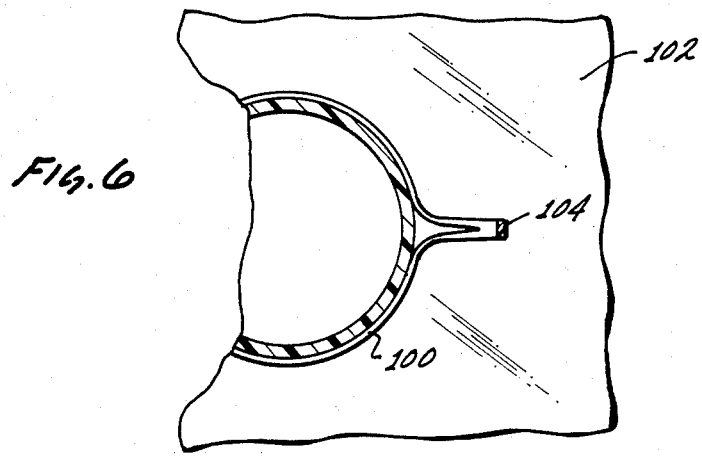

CONTAINER FOR SHARPS

This invention relates to containers for holding sharp objects such as needles. The invention particularly relates to containers providing for an easy and safe insertion of needles and other sharp objects into the containers for preventing any removal of the needles and other sharp objects from the container and for sealing the containers after the containers have been filled. The invention is particularly adapted to be used in hospitals and doctors' offices.

Hospitals and doctors use sharp objects with great frequency. For example, patients are injected with different types of medicines and nutrients. Patients are also injected with needles to draw blood for making tests on the patient. Patients are also injected with needles to make sutures. In practially every instance, the sharp objects such as needles are used only once and are then considered as trash after such single use.

Hospitals and doctors do not presently treat sharp objects such as needles with the respect that such objects deserve after the sharp objects have been used. This is unfortunate because patients subjected to the sharp objects often have communicable diseases. Furthermore, the materials remaining in the sharp objects, after the insertion of the sharp objects into the patients, may be septic.

Quite often hospitals and doctors throw the sharp objects into trash containers with other disposable material. Such a careless procedure may tend to be dangerous to the personnel in the hospitals and the doctor's offices, particularly since the trash is exposed. For example, such personnel may tend to insert their hands into the exposed trash for various reasons. This presents the danger that such personnel may be pricked by the sharp objects in the trash containers.

In recent years, some hospitals and doctors' offices have adopted procedures for dealing with sharp objects differently from other types of trash. For example, some hospitals and doctors offices have started to insert sharp objects into containers, such as plastic containers, which have been separately constructed for such purposes. The remaining trash has then been inserted into trash bags which have not been designed to receive such sharp objects.

The containers used in hospitals for receiving sharp objects have been designed to provide for an easy insertion of such sharp objects into the containers without offering any danger to the personnel making such insertion. Such containers have also been designed to inhibit any removal of sharp objects from the containers after the sharp objects have been inserted into the containers. The containers have been further designed to inhibit any puncturing of the container by the sharp objects in the container or any protrusion of sharp objects from the containers. Such a container is disclosed and claimed in application Ser. No. 510,050 filed by Ann L. Nelson, Evelyn J. Bogner, Paul M. Bogner and me on or about June 29, 1983, for a "Sharp Instruments Container" and assigned of record to the assignee of record of this application.

Although considerable advances have been made in containers for holding sharp objects, some problems still remain. For example, after the containers have been filled with sharp objects, the containers are often autoclaved or are heated to a temperature where the container collapses around the sharp objects to form a protective seal around the sharp objects. Before the containers are autoclaved or heated to their collapsible temperatures, it is desirable for the containers to be completely closed so that no sharp objects can fall from the containers.

This invention provides a container which eliminates the above difficulties. It provides for an easy insertion of sharp objects such as needles into the container and an inhibition against the removal of such sharp objects from the container. It also provides for a permanent closure of the container by a cap after the container has been filled with the sharp objects. This cap seals the container and prevents sharp objects from being removed from the container.

In one embodiment of the invention, a container for holding sharp objects includes a bottle having a body and a rim extending upwardly from the body and defining an opening into the body. A cap is disposed upon the rim in abutting relationship to the rim near the bottom of the rim. The rim and the cap define a detent relationship to hold the cap in irremovable relationship on the rim.

A funnel made from a relatively soft and pliant thermoplastic rubber material is disposed on the rim between the cap and the rim in sealed relationship with the cap and the rim. The funnel and the rim define a detent relationship to hold the funnel on the rim. The funnel is provided with a portion extending downwardly and inwardly into the opening in the rim at an angle to the rim. The inwardly extending portion is slitted to define a plurality of resilient leaves.

The funnel abuts the rim and the cap along the side and top of the rim and the cap. The top of the rim is shaped to define a fulcrum for pivotal movements of the funnel leaves in accordance with the transfer of the sharp objects into the bottle through the opening in the rim of the bottle. When the cap is inserted on the rim, the rim, the funnel and the cap define a permanently sealed relationship to prevent sharp objects from being removed from the bottle.

In the drawings:

FIG. 1 is a perspective view of a container constituting one embodiment of the invention for holding sharp objects;

FIG. 2 is an enlarged perspective view of a funnel constituting one of the components in the embodiment shown in FIG. 1;

FIG. 3 is an enlarged fragmentary sectional view taken substantially on the line 3—3 of FIG. 1 and shows in further detail the construction of the top of the container of FIGS. 1 and 2;

FIG. 4 is an enlarged fragmentary sectional view showing in additional detail the construction of the rim of the container when a cap has been permanently disposed on the rim to close the container;

FIG. 5 is an enlarged fragmentary section view, similar to that shown in FIG. 3, of a second embodiment of the container constituting this invention; and FIG. 6 is an enlarged fragmentary sectional view taken substantially on the line 6—6 of FIG. 5 and shows certain features of the embodiment of FIG. 5 in additional detail.

In one embodiment of the invention, a container generally indicated at 10 is provided. The container 10 includes a bottle 12 (FIG. 3) having a body portion 14, a narrowed neck 16 extending upwardly from the body portion 14 and a rim 18 at the top of the neck 16. The upper wall of the body portion 14 is preferably inclined upwardly toward the neck 16, as at 20. This insures that the bottle 12 will be strong at all positions in the bottle. The bottle 12 is preferably made from a polypropolyene material which provides maximum puncture resistance and also provides heat resistance to allow the container to be autoclaved up to 300° F.

The bottom of the rim 18 of the container 10 may be defined by a ledge 22 (see FIG. 4) which extends outwardly from the top of the neck 16 in a suitable direction such as a substantially horizontal direction. A first support portion 24 extends upwardly from the ledge 22 at an intermediate position along the length of the ledge. A detent 26 is provided in the support portion 24 at an intermediate position along the length of the support portion. The detent 26 may be sharply defined, as by a V-configuration, in a vertical section (see FIG. 4) of the bottle 12.

A second support portion 28 (FIG. 4) extends upwardly from the first support portion. The support 28 is preferably inclined inwardly as it extends upwardly. A detent 30 is provided in the second support portion 28. The detent 30 may be defined by an indented surface which is gently curved relative to the sharp definition of the detent 26. The top of the support portion 28 is provided with a plateau 32.

A funnel generally indicated at 34 is disposed on the plateau 32. The funnel 34 is provided with a side wall 36 which is disposed in abutting relationship to the support portion 28. A bead 38 is provided on the inner surface of the side wall 36 at the bottom of the side wall. The bead 38 may be gently curved to define a surface, such as a detent, compatible with the curvature of the detent 30.

A plateau portion 40 (FIG. 4) is provided on the funnel 34 at an intermediate position along the length of the funnel 34. The plateau portion 40 is adapted to be seated on the plateau 32 to locate the funnel 34 precisely relative to the rim 18. The guide portion 42 on the funnel 34 extends inwardly and downwardly from the plateau portion at a relatively shallow angle to the plateau portion. A guide portion 42 is slitted as at 46 to define a plurality of leaves 48 which are separated from one another at their inner ends to define an opening 50. The slits 46 extend to a rim 52 which is disposed a relatively short distance below the plateau portion 40 at the inner end of the plateau portion. The rim 52 provides a fulcrum for the pivotal movement of the leaves 48.

The funnel 34 may be made from a suitable material such as thermoplastic rubber (block copolymer polyester). This material is desirable since it allows the funnel to keep its resiliency after repeated insertions. The material is also soft to the touch which prevents accidental abrasions to fingers and allows the syringe to be dropped through the opening without resisting insertion. Most importantly, the material is heat resistant which allows the funnel and container to be shipped in extreme heat (over 180° F.) without losing its original shape.

A cap generally indicated at 60 (FIGS. 3 and 4) is adapted to be disposed on the bottle 12 and the funnel 34 to close the bottle. The cap 60 may be made from a suitable material such as polypropylene. This material is relatively rigid compared to the materials of the funnel 34. The cap 60 is provided with a top cover 62 and with a side wall 64 which extends downwardly from the top cover. The cap 60 has a detent 66 which has a configuration corresponding to that of the detent 26 to engage the detent 26. The side wall 64 rests on the ledge 22.

A loop 70 (FIG. 3) is provided on the top wall of the body portion 14. A strap 72 is looped around neck and at the other end is retained by a tap 76 which extends outwardly from the side wall 64 of the cap 60. The retention may be provided by the extension of the tab 76 through a slot 78 (FIG. 1) in an overhang 80 from the bottom of the cap.

The container 10 may be disposed in a convenient place in a hospital or doctors' office where sharp objects are generally used. For example, the container 10 may be disposed in a ward of a hospital where injections are generally administered or blood is withdrawn from a patient for tests. The cap 60 is not disposed on the rim 18 at such a time so that sharp objects such as a used needle 80 can be inserted into the bottle 12 through the opening 50 defined by the leaves 48. Although the opening 50 is provided with reduced dimensions relative to the dimensions of the sharp objects such as the used needle 80, the sharp objects are able to be inserted into the bottle 12 because of the resilient characteristics of the leaves 48. The relatively easy insertion of the sharp objects such as the needle 80 into the bottle 12 through the opening 50 is facilitated by the downwardly inclined disposition of the leaves 48.

The sharp objects inserted into the bottle are retained in the bottle without penetrating through the bottle. This insures that a person handling the container 10 will not be cut or injured in any way by sharp objects after the sharp objects have been inserted into the container. Furthermore, sharp objects cannot be easily removed from the bottle unless a person's hand is inserted into the bottle through the opening 50. Even then, an object cannot be easily removed from the bottle 12 because the leaves 48 oppose the upward movement of any of the sharp objects. This results in part because the downward inclination of the leaves 48 opposes any force acting to straighten the leaves into a horizontal plane or incline the leaves upwardly. These characteristics of the leaves 48 also oppose any tendency for the sharp objects in the bottle 12 to fall downwardly through the opening 50 if or when the bottle 12 should be inverted. The properties of the material forming the leaves 48 also inhibit any easy removal of sharp objects.

When the bottle 12 has become filled with sharp objects, the cap 60 is inserted on the rim 18. The cap 60 is properly inserted on the rim 18 by the disposition of the flange 88 on the cap against the ledge 22 on the rim 18. When the cap 60 has been properly inserted on the rim 18, the detent 66 engages the detent 26 on the rim 18. Since both of the detents 26 and 66 are sharply defined, the cap 60 is permanently disposed on the rim 18. This insures that the sharp objects such as the needle 80 in the bottle 12 are permanently retained in the bottle.

Upon the permanent disposition of the cap 60 on the rim 18, a seal is effectively established between the bottle 12, the funnel 34 and the cap. The seal is established because the side wall 64 abuts the support portion 24 of the rim 18 and also abuts the side wall 36 of the funnel 34. This assures that a tight relationship is maintained by the side wall 64 of the cap 60 against the support portion 24 of the rim 18 and the side wall 36 of the funnel 34 and also assures that a tight relationship is maintained between the support portion 28 of the rim 18 and the side wall 36 of the funnel 34.

After the cap 60 has been permanently disposed on the rim 18, the container 10 may be autoclaved. This assures that the container 10 and the sharp objects in the container are made sterile.

FIGS. 5 and 6 illustrate another embodiment of the invention. In this embodiment, a ring 100 is disposed around the neck of a bottle 102. A pliant strap 104 is integral at one end with the ring 100. At the other end, the strap 104 is integral with a cap generally indicated at 106. The cap 106 may correspond to the cap 60 in FIGS. 1 and 4.

Although this application has been disclosed and illustrated with reference to particular applications, the principles involved are susceptible of numerous other applications which will be apparent to persons skilled in the art. The invention is, therefore, to be limited only as indicated by the scope of the appended claims.

I claim:
1. In combination for storing sharp objects,
   a container for holding sharp objects, the container being made from a plastic material having properties that are heat resistant to autoclaving heat, the container having a rim portion,
   a funnel disposed on the rim portion of the container cover and having a central opening and a plurality of slits extending to the central opening,
   there being a first detent in the rim portion and a detent in the funnel for cooperating with the first detent in the rim portion to retain the funnel in locked relationship with the rim portion, and
   a cap disposed on the funnel and shaped to press the detent in the funnel against the detent in the rim portion.
2. The combination set forth in claim 1, including,
   a second detent in the rim portion of the container, and
   a detent in the cap in engagement with the second detent in the container.
3. The combination set forth in claim 2 wherein the second detent in the rim portion of the container is disposed below the first detent in the rim portion of the container and is shaped to prevent the removal of the cap from the rim portion of the container.
4. The combination set forth in claim 2 wherein the funnel has a first portion extending downwardly along the rim portion of the container and wherein the first portion includes the first detent portion and the funnel has a second portion disposed on the top of the rim portion of the container and the funnel has a third portion extending downwardly into the rim portion of the container and the slits extend along substantially the full length of the third portion of the funnel.
5. The combination set forth in claim 4 wherein the funnel is formed from a material providing for a relatively easy insertion of the sharp objects into the container through the rim of the container and inhibiting the removal of of the sharp objects from the container.
6. The combination set forth in claim 5 wherein the container is formed from a material resistant to autoclave temperatures when applied to the container.
7. In combination for storing sharp objects,
   a container having a body and a rim extending upwardly from the body and having an opening at the upper end of the rim, the rim being narrower than the body and being defined by a wall having a first portion extending upwardly in a substantially vertical direction and having a second portion extending upwardly from the first portion at substantially an oblique angle to the first portion, there being a detent in the second portion,
   a funnel disposed on the rim wall of the container and having a first portion disposed in contiguous relationship to the second portion of the rim wall and having a detent on the first portion of the funnel in cooperative relationship with the detent in the second portion of the rim wall to inhibit the removal of the funnel from the rim wall, the funnel also having a second portion extending from the first portion and disposed on the top of the rim wall, the funnel also having a third portion extending from the second portion into the opening in the rim at an inclined angle to the rim wall, and
   a cap disposed on the second portion of the funnel and having a first portion disposed in contiguous relationship to the first portion of the funnel and having a second portion extending from the first portion of the cap and closing the opening in the rim of the container.
8. The combination set forth in claim 7, including,
   there being a detent in the first portion of the rim wall, and
   a detent on the first portion of the cap in cooperative relationship with the detent in the first portion of the rim wall to inhibit the removal of the cap from the rim of the container.
9. The combination set forth in claim 7 wherein the rim wall of the container has a third portion extending inwardly from the second portion of the rim wall to define a plateau portion at the upper end of the rim wall and wherein the second portion of the funnel is disposed in contiguous relationship to the plateau portion of the rim wall.
10. The combination set forth in claim 9 wherein the plateau portion on the rim wall of the container is substantially horizontal and the second portion of the funnel is substantially horizontal and is seated on the plateau portion of the rim wall of the container.
11. The combination set forth in claim 7 wherein the rim of the container has an outwardly extending ledge at a position near the bottom of the rim wall and the first portion of the cap extends downwardly to a position contiguous to the ledge on the rim wall of the container.
12. The combination set forth in claim 8 wherein the rim wall of the container has a third portion extending inwardly from the second portion of the rim wall at a position near the top of such second portion to define a plateau portion and wherein the second portion of the funnel is disposed in contiguous relationship to the plateau portion and wherein the rim wall of the container has an outwardly turned ledge at a position near the bottom of the rim wall and the first portion of the cap extends downwardly to a position contiguous to the ledge on the rim wall of the container.
13. In combination for storing sharp objects,
    a cap having a top cover portion and a side wall extending downwardly from the top cover portion, the side wall having a detent,
    a container having a body and a rim extending upwardly from the body, the rim having a reduced lateral dimension relative to the body and being open for the deposit of the sharp objects into the body through the opening in the rim, the rim of the container being shaped to define a first portion extending from the body portion to abut the side wall of the cap, the first portion having a detent for receiving the detent in the side wall of the cap to prevent the cap from being removed from the rim, the rim having a second portion extending upwardly from the first portion in inwardly disposed relationship to the first portion, and a funnel disposed on the container between the container and the cap and having a side wall abutting the side wall of the cap and the second portion of the container rim for constraint by the side wall of the cap against the second portion of the container rim, the funnel having a portion extending into the opening in the rim at a shallowly inclined angle and slitted at spaced positions around its periphery to provide for the insertion of the sharp objects into the container through the opening in the rim and to inhibit the removal of the sharp objects from the container.

14. The combination set forth in claim 13 wherein the funnel defines leaves between the slits and the funnel is made from a relatively soft material to provide for the downward deflection of the leaves upon the insertion of the sharp objects into the container through the opening in the rim and the leaves are constructed to resist the removal from the container of the objects already in the container.

15. The combination set forth in claim 14 wherein the rim has a top portion inwardly disposed in a substantially horizontal direction to define a plateau and the funnel has a portion disposed on the horizontal plateau of the rim and wherein the slits extend substantially to the horizontal plateau from the positions within the rim.

16. The combination set forth in claim 15 wherein the funnel is provided with a rib at the outer periphery of the slits and the slits are bent downwardly at the shallowly inclined angle at positions internal to the rib.

17. The combination set forth in claim 13 wherein the side wall of the funnel and the first portion of the rim have substantially the same lateral disposition and the side wall of the funnel is disposed above the first portion of the rim and the side wall of the funnel and the second portion of the rim have substantially a detent relationship.

18. In combination for storing sharp objects, a container having a body and a rim extending upwardly from the body and defining an opening into the body, a cap disposed upon the rim of the container in abutting relationship to the rim near the bottom of the rim, means on the rim and the cap for defining a detent relationship to hold the cap in irremovable relationship on the rim, a funnel made from a relatively soft and pliant material and disposed on the rim of the container between the cam and the rim, and means on the funnel and the rim of the container for defining a detent relationship to hold the funnel on the rim, the funnel being provided with a portion extending inwardly into the opening in the rim of the container at an angle to the rim and the inwardly extending portion being slitted to define a plurality of resilient leaves.

19. The combination set forth in claim 18 wherein the cap is disposed relative to the funnel and the rim of the container for holding the funnel in constrained relationship on the rim to maintain a sealed relationship between the funnel, the cap and the rim.

20. The combination set forth in claim 19 wherein the funnel abuts the rim of the container and the cap along the side and the top of the rim and the cap and wherein the rim of the container is shaped at the top to define a fulcrum for pivotal movements of the leaves on the funnel in accordance with the transfer of the sharp objects into the container through the opening in the rim of the container.

21. The combination set forth in claim 20, including, means cooperative with the container and the cap for retaining the cap on the container until the disposition of the cap on the rim and for providing for the positioning of the cap to obtain the disposition of the cap on the rim of the container.

22. The combination set forth in claim 18 wherein the cap envelopes the funnel and the rim of the container and the detent relationship between the cap and the rim of the container is provided at a position below the bottom of the funnel and a detent relationship is established between the funnel and the rim of the container at a position above the detent relationship between the cap and the rim.

23. A combination as set forth in claim 2 wherein the funnel has a rim portion disposed over the rim portion in the container and the detent in the funnel is provided in the rim portion of the funnel to cooperate with the detent on the rim portion of the container to retain the funnel in locked relationship with the rim portion of the container.

24. A combination as set forth in claim 23 wherein the cap has a rim portion and the detent in the cap is disposed on the rim portion of the cap to provide an engagement between the rim portion on the cap and the second detent on the container.

25. The combination set forth in claim 24 wherein the rim portion on the cap is shaped to press the detent on the rim portion of the funnel against the first detent on the rim portion of the container, and the second detent in the rim portion of the container is disposed below the first detent in the rim portion of the container and is shaped to prevent the removal of the cap from the rim portion of the container.

26. A combination as set forth in claim 8 wherein the first portion on the cap presses the detent on the first portion of the funnel against the detent on the second portion of the rim wall of the container.

27. A combination as set forth in claim 17 wherein the side wall of the cap presses the side wall on the funnel against the second portion of the rim of the container to facilitate the cooperative relationship between the detent on the side wall of the funnel and the detent on the second portion of the rim of the container.

28. The combination set forth in claim 22 wherein the cap envelopes the funnel in a press-fit relationship with the funnel to facilitate the detent relationship between the funnel and the rim of the container.

29. The combination set forth in claim 28 wherein the funnel is shaped at positions laterally external to the leaves in the funnel to provide for a displacement of the funnel by sharp objects only at the positions of the leaves of the funnel.

30. The combination set forth in claim 28 wherein the detent relationship between the cap and the rim of the container is laterally external to the detent relationship between the funnel and the rim of the container.

* * * * *